United States Patent [19]

Malz, Jr. et al.

[11] 3,965,174

[45] June 22, 1976

[54] PROCESS FOR PREPARING N,N-DISUBSTITUTED ACID HYDRAZIDES

[75] Inventors: Russell E. Malz, Jr., Naugatuck; Roger W. Amidon, Oxford; Harold Greenfield, Watertown, all of Conn.

[73] Assignee: Uniroyal, Inc., New York, N.Y.

[22] Filed: July 16, 1975

[21] Appl. No.: 596,544

[52] U.S. Cl. .......................................... 260/561 H
[51] Int. Cl.² ........................................ C07C 103/32
[58] Field of Search .............................. 260/561 H

[56] References Cited

UNITED STATES PATENTS 3,062,881  11/1962  Gutmann ..................... 260/561 H

*Primary Examiner*—C. Davis
*Attorney, Agent, or Firm*—Bruce F. Jacobs

[57] ABSTRACT

A process for preparing N',N'-disubstituted acid hydrazides by reacting N'-monosubstituted acid hydrazides with aldehydes in the presence of hydrogen and a hydrogenation catalyst is disclosed.

15 Claims, No Drawings

PROCESS FOR PREPARING N,N-DISUBSTITUTED ACID HYDRAZIDES

Acid hydrazides have considerable biological activity and pharmaceutical utility as antitubercular agents, blood pressure lowering agents, and as central nervous system stimulation agents useful for relief of disturbed or depressed states. In addition, these compounds are valuable chemical intermediates in the manufacture of unsymmetrical disubstituted hydrazines by simple and high yield transformations of the corresponding acid hydrazide using such reactions as hydrolysis or transamination.

The conventional process for manufacture of unsymmetrical disubstituted hydrazines entails the reduction of an N-nitroso secondary amine. For example, methods are described in U.S. Pat. Nos. 3,187,051, June 1, 1965 (Mock); 3,102,887, Sept. 3, 1963 (Thatcher), and 3,182,086, May 4, 1965 (Levering et al.), all employing N-nitroso secondary amines as the starting materials. However, these nitrosoamines are known to be carcinogenic in nature, and the present invention avoids the use of such materials potentially harmful to human health.

It is therefore the object of this invention to provide a process for the preparation of N',N'-disubstituted acid hydrazides of the formula $R(CONR^1NR^2R^3)_n$, wherein R is hydrogen, a mono- or divalent hydrocarbyl group or a single bond, $R^1$ is hydrogen or hydrocarbyl radical, $R^2$ and $R^3$ are each hydrocarbyl radicals, and $n$ has a value of 1 or 2 corresponding to the valence of R. The process herein entails the interaction of N'-monosubstituted acid hydrazides of the formula $R(CONR^1NHR^2)_n$ wherein R, $R^1$, $R^2$ and n have the meanings above, with an aldehyde in the presence of hydrogen and a hydrogenation catalyst.

It is the further object of this invention to provide a facile method for the preparation of N',N'-disubstituted acid hydrazides without the use of known carcinogenic precursors.

The N', N'-disubstituted acid hydrazides which may be prepared in accordance with this invention have the formula $R(CONR^1NR^2R^3)_n$, wherein $n$ has a value of 1 or 2. When $n$ is 1, R is hydrogen or an alkyl group having from 1 to 18 carbons, a cycloalkyl radical having 5 to 8 carbon atoms, an aryl radical of from 6 to 12 carbons, or an aralkyl or alkaryl group having 7 to 10 carbons; usually R is an alkyl radical of from 1 to 4 carbon atoms, cycloalkyl having 5 to 6 carbon atoms, an aralkyl radical having 7 carbons, or an alkaryl group having 7 to 9 carbon atoms; most preferably R is selected from the group consisting of methyl, ethyl, propyl, isopropyl, cyclohexyl, phenyl tolyl and benzyl; $R^1$ may be hydrogen or lower alkyl with 1 to 6 carbon atoms, preferably hydrogen, methyl, ethyl or propyl, and usually hydrogen; $R^2$ has the same meanings as R except that it may not be hydrogen, and $R^3$ is a primary linear or branched alkyl group having from 1 to 18 carbon atoms, usually from 1 to 4 carbon atoms, or benzyl. When $n$ equals 2, $R^1$, $R^2$ and $R^3$ have the meanings above, and R is a single covalent bond or an alkylene radical having from 1 to 10 carbon atoms, a cycloalkylene radical having 5 to 6 carbon atoms, an alkarylene radical of from 7 to 9 carbons, an aralkylene radical having 7 to 8 carbon atoms, or a group having the formula $-C_6H_4-A-C_6H_4-$, wherein A is $-O-$, $-SO_2-$, $-CH_2-$ or $-C(CH_3)_2-$; usually R is ethylene, propylene, butylene, phenylene or tolylene. In most cases $n$ has the value of 1.

The starting materials of this invention include the N'-monosubstituted acid hydrazides of the formula $R(CONR^1NHR^2)_n$ wherein R, $R^1$, $R^2$ and $n$ have the meanings described above, (which may be prepared in situ from a non-substituted acid hydrazide or an acid hydrazone) and an aldehyde, i.e., a compound of the formula $R^4CHO$, wherein $R^4$ is selected from hydrogen, a linear or branched primary, secondary or tertiary alkyl radical having from 1 to 17 carbon atoms, or phenyl; preferably the aldehyde is selected from the group consisting of formaldehyde, acetaldehyde, propionaldehyde, n-butyraldehyde and isobutyraldehyde. These aldehydes may be employed in either a pure, oligomeric state or hydrated states such as paraformaldehyde or formalin.

The monosubstituted acid hydrazides are well known to the art and may be readily prepared as taught in such as U.S. Pat. No. 2,970,159. Jan. 31, 1961 (Gutmann et al.), also according to Yale et al. Chemotherapy of Experimental Tuberculosis, Journal of the American Chemical Society 75, 1933–1941 (1953), and Fox et al. Synthetic Tuberculostats, Journal of Organic Chemistry 18, 994–1002 (1953), all incorporated by reference herein.

The reductive alkylation is performed with a hydrogenation catalyst such as transition metals of group VIII of the Periodic Table, also metals such as copper and rhenium and sulfides and oxides thereof, copper chromite, and preferably platinum and palladium. Suitable catalysts may be either unsupported or supported on a carrier such as carbon, alumina, silica, silica alumina, alkaline earth carbonates, kieselguhr, zeolites, pumice, clay, cellulose, asbestos, etc. They may be used as powders for slurry reactions or as pellets, spheres, or granules for fixed bed reactions.

If so desired, e.g., for improved heat transfer and control of the reaction conditions, a solvent inert to the reactants may be used such as water or an organic solvent such as hexane, cyclohexane, benzene, toluene, or an aliphatic alcohol such as methanol, ethanol and isopropanol or mixtures thereof. The choice of solvent will depend usually on the solubility of both the reactants and the product in the said solvents.

The molar ratio of aldehyde to the N'-monosubstituted acid hydrazide is usually from 10/1 to 1/1, preferably between 3/1 and 1/1, and most preferably from 1.5/1 to 1/1. The catalyst concentration for batch type reactions generally may be from 0.1 to 50 parts, usually from 0.1 to 10 parts, and most preferably from 0.5 to 5 parts of active catalyst per 100 parts of said monosubstituted acid hydrazide, all parts being by weight.

The presence of a solvent is not critical although it is preferred to carry out the reaction in a diluent. Normally the volume ratio of solvent to total reactants, i.e., to said monosubstituted acid hydrazide plus the aldehyde, may vary from 0.2/1 to 50/1, usually for 0.3/1 to 5/1, and most preferably from 0.5/1 to 2/1.

The hydrogen pressure required for performing the process of this invention may range from atmospheric to a pressure of as high as 10,000 psig but usually is limited to from 10 to 5,000 psig, and the reaction may be carried out quite efficiently at pressures ranging from 100 to 2,500 psig.

The process may be conducted over a fairly broad temperature range, i.e., from about 10° to 200°C. or higher. Usually the temperature is from about 20° to 150°C., most preferably 20° to 130°C.

The process of this invention may be conducted in a batch type, semi-continuous or continuous fashion in tank or pipe-line type reactors. When applying a batch type process usually the monosubstituted acid hydrazide, aldehyde, catalyst and, optionally, solvent are first charged to the reactor. The reaction vessel is then thoroughly purged first with an inert gas such as nitrogen or helium, and then with hydrogen. Thereafter, optionally while agitating the reaction mixture, the reactor is pressurized with hydrogen to the desired pressure, agitation is started or continued, and heat is applied, if necessary, to bring the contents to the selected reaction temperature. During the course of the reaction, which may take from less than 30 minutes to 48 hours, ordinarily from 2 hours to 24 hours for this type of reaction, a drop in the hydrogen pressure is observed, and additional hydrogen may be introduced incrementally to compensate for the loss of pressure due to reaction.

It shall be appreciated by one skilled in the art that the reaction periods may vary greatly depending on the reaction system employed, e.g., in a continuous, fixed bed type process the residence time of the active ingredients may range from seconds to minutes.

When substantially no further reduction of hydrogen pressure is noticeable, the reactor is cooled, and excess hydrogen is released. The contents are removed from the reactor and filtered in order to remove the catalyst. The solvent and lower boiling materials are distilled off the reaction product in the usual manner. If the residue contains a solid N',N'-disubstituted acid hydrazide and possible by-products it may be recrystallized from solution and finally dried at a slightly elevated temperature in vacuo. If said disubstituted acid hydrazide is a liquid under ordinary conditions further purification may be achieved by distillation, chromatography or other suitable means.

If so desired, the preparation of the N',N'-disubstituted acid hydrazides according to the process of this invention may also be accomplished by reacting a nonsubstituted acid hydrazide or an acid hydrazone with an aldehyde in the presence of hydrogen and a suitable hydrogenation catalyst. All of the reaction parameters are essentially the same as disclosed herein except that for a non-substituted hydrazide the molar ratio of aldehyde to same should be at least two to one.

The following examples serve to illustrate specific embodiments of this invention but are to be understood not to limit this invention in any way.

EXAMPLE I

Preparation of N'-methyl-N'-ethylacethydrazide

A. Reductive alkylation of N'-ethylacethydrazide with formaldehyde using paraformaldehyde A mixture of 15.3 g (0.15 mole) of N'-ethylacethydrazide, 6.3 g (0.20 mole) of 97% paraformaldehyde, 94 ml of methanol and 4.8 g of 5% palladium-on-carbon (containing 50% water) was added to a 300 ml Magne Drive autoclave. The vessel was sealed, purged first with nitrogen, then with hydrogen, and pressurized with hydrogen to 700 psig. While agitating, the autoclave was heated to 60° and was kept at that temperature for 1.2 hrs., within which period the pressure dropped to 450 psig. The autoclave was cooled and depressurized. The reaction mixture was removed and filtered through diatomaceous earth to remove the catalyst. The solvent was distilled off by means of a rotary evaporator under reduced pressure at steam bath temperature, and the liquid product was treated in benzene with gaseous hydrogen chloride. A semi-solid material weighing 20.8 g (100% yield) was obtained on removing the solvent on a rotary evaporator at steam bath temperature under reduced pressure. This was slurried with acetone. The crystals were filtered off and dried over calcium sulfate in a vacuum dessicator overnight. The N'-methyl-N'-ethylacethydrazide hydrochloride had a melting point of 122°–123°.

| Analysis % | Calculated | Found |
|---|---|---|
| C | 39.35 | 38.69 |
| H | 8.59 | 8.63 |
| N | 18.35 | 17.93 |
| Cl | 23.23 | 23.20 |

B. Reductive alkylation of N'-ethylacethydrazide with formaldehyde using formalin A mixture of 15.3 g (0.15 mole) of N'-ethylacethydrazide, 16.2 g (0.21 mole) 37% formalin, 97 ml of water and 2.4 g 5% platinum-on-carbon was added to a 300-ml Magne Drive autoclave. The vessel was sealed, purged first with nitrogen, then with hydrogen, and pressurized with hydrogen to 800 psig. The autoclave was heated with agitation at 60°–65° and 600–800 psig for 6.0 hours. The vessel was cooled and depressurized. The reaction mixture was removed and filtered through diatomaceous earth to remove the catalyst. Most of the water was distilled off and benzene was added. The benzene solution was dried by azeotropic distillation using a Dean-Stark apparatus. Gaseous hydrogen chloride was bulled through this benzene solution resulting in the precipitation of the hydrochloride compound as a white powder which was filtered off. The N'-methyl-N'-ethylacethydrazide hydrochloride was reslurried with acetone, filtered and dried as in Example IA, and 12.5 g (55% yield) of material was recovered having a melting point of 120°–121.5°C. No change in melting point was observed when a portion of this product was mixed with a portion of that of Example IA.

The above benzene and acetone filtrates were combined and stripped on a rotary evaporator under reduced pressure at steam bath temperature, and an additional 7.3g (32% yield) of a crude solid product was obtained.

EXAMPLE II

Preparation of N',N'-diethylacethydrazide

A. Acylation of N,N-diethylhydrazine with acetic anhydride

N',N'-diethylacethydrazide was prepared following essentially the teaching of Hinman and Fulton, J. Amer. Chem. Soc. 80, 1895–1900 (1958). A mixture of 8.2 g (0.094 mole) of freshly distilled N,N-diethylhydrazine and 75 ml of benzene was added to a three-necked 250-ml round bottom flask equipped with a stirrer, a thermometer and a pressure equilibrating addition funnel capped with a drying tube. The flask was cooled in an ice bath. To this stirred solution was added 12.3 g (0.12 mole) of acetic anhydride. The ice bath was removed and the reaction mixture was heated for 1 hr. at 48°–58°. A fractional distillation of the reaction mixture gave a cut, b.p. 83°–84° at 3 mm, which melted at 47.5°–49.5°. NMR (CCl$_4$, TMS) τ 1.0 (3 H, t), 1.9 (3 H, s), 2.6 (2 H, quad), 8.5 (1 H, broad).

| Analysis % | Calculated | Found |
|---|---|---|
| C | 55.35 | 55.35 |
| H | 10.84 | 10.76 |
| N | 21.52 | 21.30 |

A portion of the N',N'-diethylacethydrazide was treated in benzene with gaseous hydrogen chloride resulting in the precipitation of a white crystalline hydrochloride. The product was filtered and washed with hexane. The melting point of the N',N'-diethylacethydrazide hydrochloride, after air drying overnight, was 189.5°–192°.

| Analysis % | Calculated | Found |
|---|---|---|
| C | 43.24 | 43.39 |
| H | 9.07 | 9.20 |
| N | 16.81 | 16.65 |
| Cl | 21.27 | 21.22 |

B. Reductive alkylation of N'-ethylacethydrazide with acetaldehyde

A mixture of 15.3 g. (0.15 mole) of N'-ethylacethydrazide, 8.8 g (0.20 mole) of acetaldehyde, 90 ml of methanol and 4.8 g of 5% palladium-on-carbon (containing 50% water) was added to a 300-ml Magne Drive autoclave. Thereafter the autoclave was purged and pressurized as described in Example I and heated with agitation at 30°–35° and 465–700 psig for 1.7 hrs. The vessel was cooled and depressurized. The reaction mixture was removed and filtered through diatomaceous earth to remove the catalyst. Removal of the solvent on a rotary evaporator under reduced pressure at steam bath temperature and drying over calcium sulfate in a vacuum dessicator overnight gave 20.0 g (102% yield) of a white crystalline residue that melted at 46°–49.5°. Treatment of a benzene solution of this N',N'-diethylacethydrazide with gaseous hydrogen chloride gave a precipitate of N',N'-diethylacethydrazide hydrochloride. This was filtered, washed with hexane and air dried. It melted at 187°–189°. There was no depression on a mixed melting point with a sample from Example IIA.

EXAMPLE III

Preparation of N'-methyl-N'-isopropylacethydrazide by reductive alkylation of N'-isopropylacethydrazide with formaldehyde Following essentially the same procedure as in Example I, 14.3 g (0.12 mole) of N'-isopropylacethydrazide, 6.2 g (0.20 mole) of 97% paraformaldehyde, 96 ml of methanol and 4.8 g of 5% palladium-on-carbon (containing 50% water) were pressurized with hydrogen to 600 psig. The vessel was then agitated at 30° and 375-600 psig for 5 hrs. The vessel was emptied and the catalyst removed in the previous manner. The mixture was diluted with benzene and concentrated on a hot plate. The benzene solution, essentially free of methanol, was mixed with chilled hexane to about three times its original volume. The oil that separated was taken off in a separatory funnel. A thin layer chromatography (TLC) indicated a substantially pure product with only a trace amount of unknown impurity. A small portion of the oil was chromatographed through a silica gel column with a 95/5 toluene/methanol eluent to give a fraction showing only the main component by TLC. This fraction was concentrated, thus removing most of the methanol, and treated with gaseous hydrogen chloride. After slurrying with acetone, filtering and drying as in Example IA, the N'-methyl-N'-isopropylacethydrazide hydrochloride melted at 170°–171°.

| Analysis % | Calculated | Found |
|---|---|---|
| C | 43.24 | 42.77 |
| H | 9.07 | 8.83 |
| N | 16.81 | 16.22 |
| Cl | 21.27 | 20.71 |

EXAMPLE IV

Preparation of N',N'-dimethylacethydrazide.

A. Acylation of N,N,-dimethylhydrazine with acetic anhydride

The procedure used herein is the same as in Example IIA.

A mixture of 18.0 g (0.30 mole) N,N-dimethylhydrazine and 50-ml of benzene was added to a three-necked 250-ml. round bottom flask equipped as in Example IIA. The flask was cooled in an ice bath. To this stirred solution was added 40.8 g (0.4 mole) acetic anhydride at a rate such that the temperature remained below 40°. The solvent was stripped on a rotary evaporator at reduced pressure while heating on a steam bath. The residue was fractionated to give a cut distilling at 98°–99° at 16 mm. TLC of this product indicated only one spot. A portion of the N',N'-dimethylacethydrazide was dissolved in benzene and gaseous hydrogen chloride bubbled through. A white precipitate formed which was filtered, washed with hexane, and dried over calcium sulfate in a vacuum dessicator. The dry N',N'-dimethylacethydrazide hydrochloride melted at 167°–168°.

| Analysis % | Calculated | Found |
|---|---|---|
| C | 34.67 | 34.46 |
| H | 8.00 | 8.05 |
| N | 20.21 | 20.16 |
| Cl | 25.58 | 25.20 |

B. Reductive alkylation of N'-methylacethydrazide with formaldehyde using a palladium catalyst A mixture of 10.0 g (0.113 mole) N'-methylacethydrazide, 6.2 g (0.20 mole) 97% paraformaldehyde, 100 ml of 2-propanol and 5.0 g of 5% palladium-on-carbon (containing 50% water) was added to a 300-ml Magne Drive autoclave. The vessel was purged as in Example IA, pressurized with hydrogen to 800 psig and heated with agitation at 60°–65° and 680 to 840 psig for 0.75 hrs. The vessel was cooled and depressurized. The vessel was emptied and the catalyst removed by filtration through diatomaceous earth. The solution was diluted with toluene and then concentrated on a hot plate to remove most of the water and 2-propanol. Gaseous hydrogen chloride was bubbled through this toluene solution resulting in a light yellow crystalline precipitate. This was filtered and washed with benzene. After drying as in Example IA, 14.1 g (90% yield) of N',N'-dimethylacethydrazide, m.p. 156°-162°, was obtained. A 5.5 g portion was taken and slurried with acetone, filtered and dried as in Example IA, and 5.1 g of material, m.p. 163°-165°, was obtained. There was no depression on a mixed melting point with a sample as prepared in Example IVA.

C. Reductive alkylation of N'-methylacethydrazide with formaldehyde using a platinum catalyst A mixture of 9.4 g (0.11 mole) N'-methylacethydrazide, 6.2 g (0.20 mole) 97% paraformaldehyde, 103 ml of 2-propanol and 2.5 g 5% platinum-on-carbon was added to a 300-ml Magne Drive autoclave. The vessel was purged as in Example IA, pressurized with hydrogen to 800 psig, and heated with agitation at 50°-55° and 700-840 psig for 3.5 hrs. The vessel was cooled and depressurized. The reaction mixture was removed and the catalyst filtered from it using diatomaceous earth. The solution was diluted from 300 ml to 600 ml with toluene and then concentrated to 200 ml on a hot plate to remove most of the 2-propanol. Gaseous hydrogen chloride was bubbled through the toluene solution. The resulting light yellow precipitate was filtered, washed with a little benzene and acetone, and then dried as in Example IA, and gave 11.6 g (78% yield) N',N'-dimethylacethydrazide hydrochloride which melted at 155°-161°. A 7.0 g portion was slurried with acetone, filtered and dried as in Example IA. It yielded 6.6 g which had a m.p. of 163°-165°. When this was mixed with a sample from Example IVA, no depression of the melting point was observed.

D. Preparation of N',N'-dimethylacethydrazide from 2-methyleneacethydrazide

A mixture of 12.9 g (0.15 mole) 2-methyleneacethydrazide, 16.2 g (0.20 mole) 37% formalin, 93 ml of water and 5.0 g 5% palladium-on-carbon (containing 50% water) was added to a 300-ml Magne Drive autoclave. The vessel was purged as in Example IA and pressurized to 800 psig. The autoclave was heated with agitation at 60°14 65° and 600-900 psig for 10.3 hrs. The vesesel was cooled and depressurized. The reaction product was removed and filtered through diatomaceous earth to remove the catalyst. Most of the water was distilled off and benzene was added. The benzene was dried by azeotropic distillation. A TLC showed a major spot with an $R_f$ identical to the N',N'-dimethylacethydrazide as prepared in Example IVA.

What is claimed is:

1. A process for preparing N',N'-disubstituted acid hydrazides of the formula

comprising reacting an N'-monosubstituted acid hydrazide of the formula

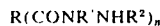

with an aldehyde of the formula $R^4CHO$ in the presence of hydrogen and a hydrogenation catalyst wherein $n$ is an integer of 1 or 2;

R is hydrogen, a monovalent hydrocarbyl group, a divalent hydrocarbyl group, or a single bond;

$R^1$ is hydrogen or a hydrocarbyl group;

$R^2$ is a hydrocarbyl group;

$R^3$ is a primary linear or branched alkyl group having 1 to 18 carbon atoms or benzyl; and $R^4$ is hydrogen, a linear or branched primary, secondary or tertiary alkyl group having 1 to 17 carbon atoms or phenyl.

2. The process of claim 1 wherein the hydrogenation catalyst is selected from platinum and palladium.

3. The process of claim 2 wherein the hydrogenation catalyst is platinum.

4. The process of claim 2 wherein the hydrogenation catalyst is palladium.

5. The process of claim 1 wherein the molar ratio of aldehyde to N'-monosubstituted acid hydrazide is from 10/1 to 1/1.

6. The process of claim 1 wherein the molar ratio of aldehyde to N'-monosubstituted acid hydrazide is from 3/1 to 1/1.

7. The process of claim 1 wherein the pressure is from atmospheric pressure to 10,000 psig.

8. The process of claim 1 wherein the pressure is from 10 to 5000 psig.

9. The process of claim 1 wherein the temperature is from 10° to 200°C.

10. The process of claim 1 wherein the temperature is from 20° to 150°C.

11. The process of claim 1 wherein a solvent inert to the reactants is included.

12. The process of claim 11 wherein the solvent is selected from the group consisting of water, hexane, cyclohexane, benzene, toluene, methanol, ethanol, isopropanol, or mixtures thereof.

13. The process of claim 2 wherein the catalyst is supported on a carrier.

14. The process of claim 1 wherein the aldehyde is selected from the group consisting of formaldehyde, actaldehyde, propionaldehyde, n-butyraldehyde, isobutyraldehyde, paraformaldehyde, and formalin.

15. The process of claim 2 wherein the active catalyst is present in from 0.1 to 50 parts by weight per 100 parts of monosubstituted acid hydrazide.

* * * * *